(12) United States Patent
Pena De Sousa Santos et al.

(10) Patent No.: US 10,341,575 B2
(45) Date of Patent: *Jul. 2, 2019

(54) METHOD AND SYSTEM FOR CAPTURING IMAGES OF A LIQUID SAMPLE

(71) Applicant: BIOSURFIT, S.A., Aveiro (PT)

(72) Inventors: David Pena De Sousa Santos, Beja (PT); Miguel João Marques Barreiros, Lisbon (PT); Fábio Miguel Rolo Pereira, Lisbon (PT)

(73) Assignee: Biosurfit, S.A., Aveiro (PT)

( * ) Notice: Subject to any disclaimer, the term of this patent is extended or adjusted under 35 U.S.C. 154(b) by 0 days.

This patent is subject to a terminal disclaimer.

(21) Appl. No.: 15/947,321

(22) Filed: Apr. 6, 2018

(65) Prior Publication Data

US 2018/0234609 A1    Aug. 16, 2018

Related U.S. Application Data

(63) Continuation of application No. 15/532,091, filed as application No. PCT/EP2017/058097 on Apr. 5, 2017.

(30) Foreign Application Priority Data

Apr. 6, 2016  (GB) .................................. 1605897.6
Apr. 6, 2016  (PT) ........................................ 109297

(51) Int. Cl.
G06K 9/00     (2006.01)
G06T 7/20     (2017.01)
(Continued)

(52) U.S. Cl.
CPC ....... H04N 5/2356 (2013.01); G01N 15/1459 (2013.01); G01N 15/1463 (2013.01);
(Continued)

(58) Field of Classification Search
CPC ........... G06T 7/579; G06T 7/571; G06T 7/20; G01N 15/1459; G01N 15/1463; H04N 5/2359

See application file for complete search history.

(56) References Cited

U.S. PATENT DOCUMENTS 8,831,306 B2    9/2014  Manri et al.
8,988,520 B2 *  3/2015  Liu .................. G02B 21/367
                                                        348/355

(Continued)

FOREIGN PATENT DOCUMENTS

EP          0486747 A2    5/1992
WO    WO 2016/050755 A1  4/2016
WO    WO 2016/050767 A1  4/2016

OTHER PUBLICATIONS

PCT International Search Report and Written Opinion for PCT/EP2017/058097, dated Jun. 8, 2017, 16 pages.

(Continued)

*Primary Examiner* — Kim Y Vu
*Assistant Examiner* — Molly Delaney
(74) *Attorney, Agent, or Firm* — Patterson Thuente Pedersen, P.A.

(57) ABSTRACT

A method and system for capturing images of a liquid sample flowing through a field of view of an imaging device that can include stepping a focus mechanism of the imaging device through a plurality of focus values and capturing a plurality of images of the sample at each of the plurality of focus values as the sample flows through the field of view of the imaging device. In this way, image capture can proceed before a focus value has been determined and capture images that are in focus can be used for further processing subsequently.

11 Claims, 4 Drawing Sheets

(51) Int. Cl.
*G01N 15/10* (2006.01)
*G01N 15/14* (2006.01)
*G06T 7/571* (2017.01)
*G06T 7/579* (2017.01)
*H04N 5/235* (2006.01)

(52) U.S. Cl.
CPC ............ *G06K 9/00134* (2013.01); *G06T 7/20* (2013.01); *G06T 7/571* (2017.01); *G06T 7/579* (2017.01); *G01N 2015/1075* (2013.01); *G01N 2015/1447* (2013.01); *G01N 2015/1452* (2013.01); *G01N 2015/1497* (2013.01)

(56) References Cited

U.S. PATENT DOCUMENTS

| | | | |
|---|---|---|---|
| 9,470,618 B2* | 10/2016 | Farrell | G01N 15/1404 |
| 2004/0217256 A1 | 11/2004 | Ortyn et al. | |
| 2005/0127271 A1* | 6/2005 | Ortyn | G01N 15/1459 250/201.4 |
| 2007/0279365 A1* | 12/2007 | Kageyama | G02B 7/38 345/100 |
| 2009/0213239 A1 | 8/2009 | Yoshida | |
| 2010/0308205 A1* | 12/2010 | Chang | G02B 21/244 250/201.3 |
| 2011/0157344 A1* | 6/2011 | Xie | G02B 7/38 348/61 |
| 2012/0127297 A1* | 5/2012 | Baxi | G06T 7/0002 348/79 |
| 2014/0273067 A1 | 9/2014 | Wanders et al. | |
| 2014/0273068 A1* | 9/2014 | Wanders | G01N 33/5094 435/29 |

OTHER PUBLICATIONS

Irwin Sobel, "An Isotropic 3 3 Image Gradient Operator, History and Definition of the so-called Sobel Operator", Feb. 2, 2014, updated Jun. 14, 2015, 6 pages http://www.researchgate,net/publication/239398674_An_Isotropic_3_3_Image_ Gradient_Operator.
Portugal Search Report for Application No. 109297, dated Sep. 21, 2016, 4 pages.

* cited by examiner

METHOD AND SYSTEM FOR CAPTURING IMAGES OF A LIQUID SAMPLE

CROSS-REFERENCE TO RELATED APPLICATIONS

This application is a continuation application of U.S. patent application Ser. No. 15/532,091, filed May 31, 2017 which is a National Phase entry of PCT Application No. PCT/EP2017/058097, filed Apr. 5, 2017, which claims priority from Great Britain Application No. 1605897.6 filed Apr. 6, 2016 and which claims priority from Portugal Application No. 109297, filed Apr. 6, 2016, the disclosures of which are all hereby incorporated by referenced herein in their entirety.

TECHNICAL FIELD

The present invention relates to a method and system for capturing images of a liquid sample during flow.

BACKGROUND

Some methods of analyzing a liquid sample involve capturing images of the sample whilst the sample is flowing. Characteristics of the sample can then be determined based on the captured images. In order to accurately determine these characteristics, it is desirable to focus the imaging device on the sample and, in particular, where appropriate, the component of the sample which is of interest. For example, if the sample is a blood sample, it may be desirable to focus the imaging device on blood cells or platelets in particular.

One approach to obtaining images of the sample which are in focus is to carry out a focusing algorithm in order to focus the imaging device on the sample once the sample has started flowing. However, this typically takes dozens of seconds or even minutes.

SUMMARY

Aspects of the disclosure are set out in the independent claims. Further, additional features are set out in the dependent claims.

In some aspects, there is provided a method of capturing images of a liquid sample flowing through a field of view of an imaging device. The method comprises stepping a focus mechanism of the imaging device through a plurality of focus values and capturing a plurality of images of the sample at each of the plurality of focus values as the sample flows through the field of view of the imaging device.

Advantageously, the method reduces or even eliminates the time spent on focusing an imaging device on the liquid sample during flow before images are captured in order to increase the amount of time available for image capture. Specifically, by capturing a plurality of images at each of a plurality of focus values, a set of images of the liquid sample over time is obtained at multiple focus values. In other words, a data set (i.e. a set of images over time) is obtained for each of the plurality of focus values. The images in which the liquid sample is in focus can then be selected and used to carry out analysis on the liquid sample. Capturing multiple sets of images, each at a different focus value, thus avoids the need for a preliminary step of finding a suitable focus value for the image capture device before data collection begins. Instead, image capture can begin as soon as the liquid sample begins to flow.

In some embodiments, stepping the focus mechanism through the plurality of focus values comprises repeatedly varying the focus value between a minimum value and a maximum value. Advantageously, this means that images captured at a given focus value are spread out over time more than they would be if the focus value would be increased stepwise, with a first set of images taken at a first focus value, then a second set of images at a second focus value and so on. During this longer time period, a greater volume of liquid flows through the field of view of the imaging device and as a result, a greater number of objects (e.g. blood cells or platelets) are imaged at a given focus value. Conversely, in the step-wise method, images taken at a given focus value are clustered together in time and span a smaller volume of liquid and hence fewer objects are imaged at a given focus value.

In some embodiments, stepping the focus mechanism through the plurality of focus values comprises varying the focus value periodically.

In some embodiments, consecutive images are captured at different focus values. In other words, each image is captured at a focus value which is different to that at which the previous image was captured.

In some embodiments, a focus measure is determined for each of some or all of the captured images. A focus measure may refer to a value of any quantity which is indicative of whether, and optionally to what extent, a given image is in focus. In some embodiments, the focus measure is a contrast-based focus measure. For example, a Sobel operator may be used to derive the focus measure by convoluting the operator with captured pixels. See for example, "An Isotropic 3×3 Image Gradient Operator" by Irwin Sobel published Feb. 2, 2014 and available online at researchgate.net. For example, focus measures may be calculated by convoluting the operator with image patch or patches around segmented objects. In some embodiments, the operator is applied to the whole image. Other operators may also be used to calculate the focus measure, as is well known in the art.

In some embodiments, a velocity of one or more objects in an image may be determined and a focus measure for the image determined based on the velocities.

In some embodiments, determining a focus measure may include identifying and counting objects within each image and determining a focus measure for each image based on the number and/or type and/or size of objects identified in that image. For example, objects may be platelets in a blood sample. Determining a focus measure in this way is based on the idea that, generally, the most objects being counted will be found in the images which are most in focus. Taking the example of counting platelets, images may be captured for the purpose of determining a platelet count. Once the images have been captured, an algorithm is used to identify and count the platelets in each image. For the images in which the platelets appear but are out of focus, the platelets may not be identified and counted as platelets by the algorithm. On the other hand, platelets in the in-focus images would be identified and counted by the algorithm as platelets. In this way, the number of objects of interest which are identified in each image may be indicative of whether, and optionally to what extent, that image is in focus.

In some embodiments, a subset of images for further processing is identified. Further processing may involve saving the images, sending them to a different processor for analysis, or carrying out analysis on the images, for example to determine a characteristic of the sample. In the event that the sample is a blood sample, such a characteristic may be a blood cell count or a platelet count.

In some embodiments, further processing the images may include measuring one or more of the size, shape or colour of objects in the images. In some embodiments, it may include characterising the behaviour of objects in the images, such as aggregation of objects (e.g. blood cells or platelets), a change in shape of the objects and/or the position of objects in the flow channel.

In some embodiments, a subset of images for further processing is identified based on the focus measures of the captured images.

In some embodiments, the subset of images for further processing may be identified directly based on the focus measures of the images. For example, a focus acceptability criterion may be evaluated on the focus measure of each image and those images which have a focus measure which satisfies the criterion identified for further processing. In some embodiments, identifying a subset of the captured images includes applying a threshold to the determined focus measures. In some embodiments, identifying a subset of images for further processing includes determining a range of focus measures and identifying for further processing those images which have a focus measure falling within the range. In some embodiments, identifying a subset includes ordering the focus measures and including in the subset those images which have a focus measure in a top range of values, for example the top 5%, 10% or 20% etc. of focus measures.

In some embodiments, a subset of images may be identified for further processing based on the mean focus measure, the median focus measure, the standard deviation of the focus measures (e.g. across all captured images, or images taken at a particular focus value) or any other quantity.

In some embodiments, the subset of images for further processing may be identified based on the focus measures of the images indirectly, for example via the focus value at which each image was taken. For example, in some embodiments, identifying a subset of images for further processing includes selecting one or more focus values based on the determined focus measures and identifying for further processing images which were taken at the selected focus value(s). In some embodiments, the average focus measure across images taken at each focus value may be determined and one or more focus values selected based on the average focus measures. In some embodiments, the average focus measure may be an extremum or a local extremum.

In some embodiments, identifying a subset of images for analysis involves selecting a focus value for which the corresponding average focus measure is a local extremum and the corresponding average object velocity is larger than object velocities at any other local extrema of the determined focus measures. Methods of determining object velocities are described in application number PCT/EP2015/072416, which is incorporated by reference herein in its entirety.

In some embodiments, once images have been identified for further processing, they may be marked or flagged as belonging to the subset for further processing. Alternatively or additionally, those images which are not identified for further processing may be deleted.

In some embodiments, images are captured online, while the sample flows, and the captured images are processed offline, once all of the sample to be imaged has been imaged. In particular, in some embodiments, the steps of determining a focus measure for each image and identifying a subset of the images for further processing may be carried out offline, once all of the sample to be imaged has been imaged. In some embodiments, the captured images are processed once the whole liquid sample has flowed through the flow channel.

In some embodiments, the method may comprise determining a first focus value based on the determined focus measures, setting the focus mechanism of the imaging device according to the first focus value and capturing further images at the first focus value. In this way, image capture can begin as soon as the liquid sample starts to flow, with a plurality of images at each of a plurality of focus values being captured. These images can then be processed and a focus value selected based on these images (for example based on focus measures determined for the images). The focusing mechanism can then be set according to the selected focus value and further images captured at the selected focus value. In other words, there may be a first stage in which a plurality of images are captured at each of the plurality of focus values and a focus measure determined for each image. A focus value is then determined based on the determined focus measures and the focus mechanism of the imaging device set according to the determined focus value. One or more further images are then captured at the focus value. In some embodiments, the rest of the images may be captured at the determined focus value. In other words, further images may be captured at the focus value without changing the focus value.

In some embodiments, the method may comprise identifying for further processing the images which were captured at the selected focus value. In some embodiments, this may include the images captured at the focus value during the first stage (during which a plurality of images at each of a plurality of focus values were captured). The images captured during the first stage of image capture (during which a plurality of images at each of a plurality of focus values were captured) are used to select a focus value and also form part of the set of images on which analysis of the liquid sample is carried out. Advantageously, in this way, useful data is acquired whilst a suitable focus value is identified.

In embodiments in which the method comprises determining focus measures of captured images, the method may further comprise setting a second plurality of focus values based on the determined focus measures and/or the focus value selected based on the determined focus measures. The method may further comprise stepping the focus mechanism of the imaging device through the second plurality of focus values and capturing a plurality of images of the sample at each of the second plurality of focus values as the sample flows through a field of view of the imaging device. In this way, the focus values at which images are captured can be updated based on analysis carried out on previously captured images. For example, a range of focus values at which images are captured may be shifted over time as the images taken previously are processed and the resulting data used to optimise the focus values at which later images are captured.

In some embodiments there is provided a method of:
a. stepping the focus mechanism of the imaging device through a plurality of focus values
b. capturing a plurality of images of the sample at each of the plurality of focus values as the sample flows through the field of view of the imaging device
c. determining a focus measure for each of the images captured at each of the plurality of focus values;
d. identifying a focus value based on the determined focus measures
e. setting the focusing mechanism of the imaging device to the focus value
f. capturing further images at the focus value and g. repeating steps (a) to (e)

The method may comprise alternating phases of (1) varying the focus value and capturing images and (2) keeping the focus value constant and capturing images. In this way, a check may be carried out periodically (by varying the focus value, capturing images and analysing the images) in order to check that images are being captured at a suitable focus value. If they are not, then the focus value of the focus mechanism may be changed.

In some embodiments, the method may comprise identifying for further processing the images captured at the focus value identified initially (i.e. the first time step d is carried out) and/or the focus value identified at the first check (i.e. the second time step d is carried out).

In some embodiments, the method further comprises setting the plurality of focus values at which images are captured such that images of the liquid sample are captured across the depth of a channel in which the liquid sample flows. In other words, the plurality of focus values are set such that the set of focal planes at which images are captured spans the depth of the channel.

In some embodiments, the channel in which the liquid sample flows may be provided on a disc or cartridge, for example a microfluidic disc, which is disposed relative to the imaging device. In some embodiments, the disc or cartridge may be fixedly disposed relative to the imaging device in a direction perpendicular to the focal plane of the imaging device. In some embodiments, the disc or cartridge may be free to rotate in a plane parallel to the focal plane of the imaging device. Flow of the sample through the channel may be driven by a variety of driving mechanisms, including capillary forces, centrifugal forces, electrophoretic forces and any other suitable driving mechanisms.

In some embodiments, the channel and the imaging device may be part of the same apparatus as the imaging device.

In some embodiments, the method may comprise determining the depth of the channel through which the liquid sample flows. In some embodiments, the depth of the channel may be associated with a cartridge or disc (e.g. a microfluidic disc) on which the channel is provided. Alternatively, the depth of the channel may be stored in a memory of the device in which the imaging device is provided.

In some embodiments, once a subset of images for further processing has been identified, the method comprises carrying out the further processing of the images in the subset. As mentioned above, further processing may include saving the images in a certain location or sending them elsewhere (e.g. to a processor) for analysis. In some embodiments, further processing the images may comprise determining a characteristic of the liquid sample based on the images in the sample. For example, further processing the images may include identifying and counting objects, for example cells, within each image. Such methods of image analysis are described in more detail in application number PCT/EP2015/072392, which is incorporated herein by reference in its entirety. In some embodiments, further processing the images may include measuring one or more of the size, shape or colour of objects in the images. In some embodiments, it may include characterising the behaviour of objects in the images, such as aggregation of objects (e.g. blood cells or platelets), a change in shape of the objects and/or the position of objects in the flow channel.

In some embodiments, the method may comprise determining an object count based on the images identified for further processing.

In some embodiments, a further subset of the subset of images identified for further processing is selected based on the number of in-focus images required in order to determine an accurate object count. For example, in some embodiments, 100 images may be required to obtain an accurate object count result and as such, 100 images out of the subset originally identified for further processing are selected. Advantageously, by selecting a further subset of the subset of images identified for further processing, the chances of a given object appearing in more than one image can be reduced or even eliminated. This reduces the chances of a given object being counted more than once (by virtue of it appearing in more than one image).

In some embodiments, the further subset of images may be selected such that they are evenly spaced in time across the time period spanned by the subset of images identified for further processing.

In some embodiments, once the further subset of the subset of images identified for further processing have been selected, objects in the subset of subset of images are then identified. This may be done, for example, using standard techniques known in the art.

In some embodiments, the method may comprise determining whether any of the objects in the images remained stationary for a period of time during which images were captured (thus appearing in the same position in multiple images). This may be done, for example, by comparing two or more images and identifying any objects which appear in the same or similar position in more than one of the two or more images. Advantageously, this step may aid in avoiding counting any objects which are stuck in the field of view (i.e. are not flowing along the flow channel). This may improve the accuracy of an object count determined based on these images.

In some embodiments, the method may further comprise the steps of:

(i) determining the total number of objects in the further subset of the subset of images identified for further processing;

(ii) determining the total volume of liquid appearing in the further subset of the subset of images identified for further processing; and (iii) determining an object count based on the total number of objects in the further subset of the subset of images identified for further processing and the total volume of liquid appearing in the subset of the subset of images identified for further processing.

In some embodiments, step (i) may comprise adjusting the total number of objects in the further subset of the subset of images identified for further processing based on the number of objects having been identified as having remained stationary for a period of time during which images were captured.

In some aspects, there is provided a system for analysing a liquid sample flowing through a field of view of an imaging device. The system comprises an imaging device for imaging a liquid sample flowing through a field of view of the imaging device, wherein the imaging device has a focus mechanism for positioning at least a portion of the imaging device in accordance with a focus value. The system further comprises a processor configured to step a focus mechanism of the imaging device through a plurality of focus values and capture a plurality of images of the sample at each of the plurality of focus values as the sample flows through a field of view of the imaging device.

In some embodiments, the system may comprise a sample holder configured to receive a cartridge comprising a flow channel, the sample holder being configured to hold the cartridge relative to the imaging device. For example, the cartridge may be a disc, for example a microfluidic disc, and the holder may be a tray or slot similar to those found in DVD players.

In some embodiments, the processor may be configured to implement any of the methods as described herein or as set out in the claims.

In some embodiments, there is provided one or more tangible computer readable media configured to implement the method steps of any of the method claims or as described herein.

In some embodiments there is provided a computer program product comprising coded instructions which, when run on a processor, implement a method as claimed in any of the method claims or as described herein.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
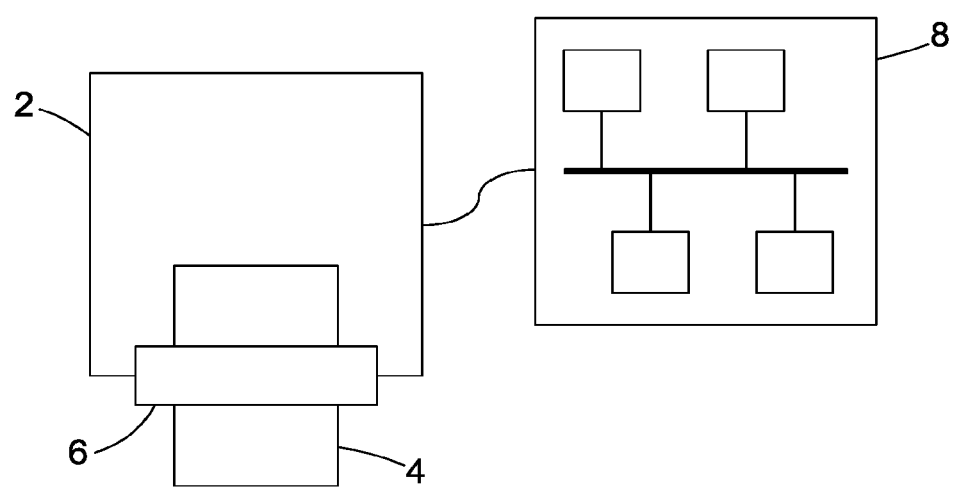
FIG. 1 is a schematic illustration of an imaging device for imaging a flowing sample.
Figure 1:
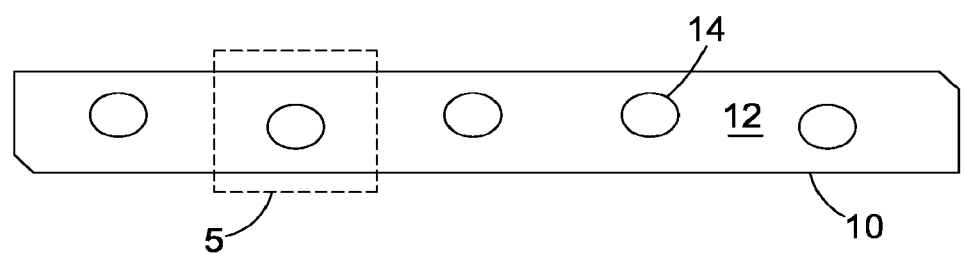

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

With reference to FIG. 1, an imaging device 2 comprises an objective (lens) assembly 4 for forming an image of a field of view 5 inside the imaging device 2. A focusing mechanism 6 is coupled to the objective assembly 4 to move the objective assembly along an optical axis in order to focus at a given depth inside the field of view. A focus value is a value indicative of where the imaging device 2 is focused. In some embodiments, the focus value is chosen to be a position along the optical axis of the objective assembly 4 relative to the imaging device 2. In some embodiments, the focus value is chosen to be a distance of an imaged plane in focus from the imaging device 2 or a value related to the configuration of the focus mechanism (e.g. rotor position of a focus drive motor) or any other value indicative of where the imaging device is focused.

A processor 8 is coupled to the imaging device 2 and receives images and other signals for processing from the imaging device 2. In turn, the processor sends control information to the imaging device 2, including control information to set a focus value and cause the focus mechanism 6 to position (or configure) the objective assembly 4 in accordance with the focus value, as well as to, in some embodiments, control one or more other parameters of the imaging device, for example the imaging gain of an image sensor inside the imaging device 2. In this embodiment, the imaging device 2 and processor 8 are housed in a single unit. In some embodiments, components of the processor 8 and imaging device 2 may be provided on a single integrated circuit. It will be understood that in some embodiments, the imaging device 2 and processor 8 may be provided as separate units.

A sample conduit 10 carries a flowing sample 12 containing objects 14. In this embodiment, the sample is a blood sample and the objects are blood cells, for example white blood cells. The objects may, in some embodiments, be platelets. The sample conduit 10 is disposed within the field of view 5, so that the sample 12 and objects 14 can be imaged by the imaging device, for example capturing a time series of frames at a given sample rate. The sample conduit 10 is disposed relative to the imaging device 2 in a manner not illustrated in FIG. 1 for clarity. The sample conduit 10 is provided on a microfluidic analysis cartridge which can be inserted into a holder associated with the imaging device 2 to dispose the sample conduit 10 relative to the imaging device 2. In some embodiments, the sample conduit 10 and imaging device 2 may form part of a single device.

The sample conduit 10 is provided on a disk cartridge implementing a lab on a disk device and the imaging device and processor are part of a DVD reader like reader device including a mechanism for loading the lab on a disk device. Flow of the sample is driven by capillary forces. In some embodiments, flow of the sample may be driven by a variety of driving mechanisms, including centrifugal forces, electrophoretic forces and any other suitable driving mechanisms.

Figure 2:
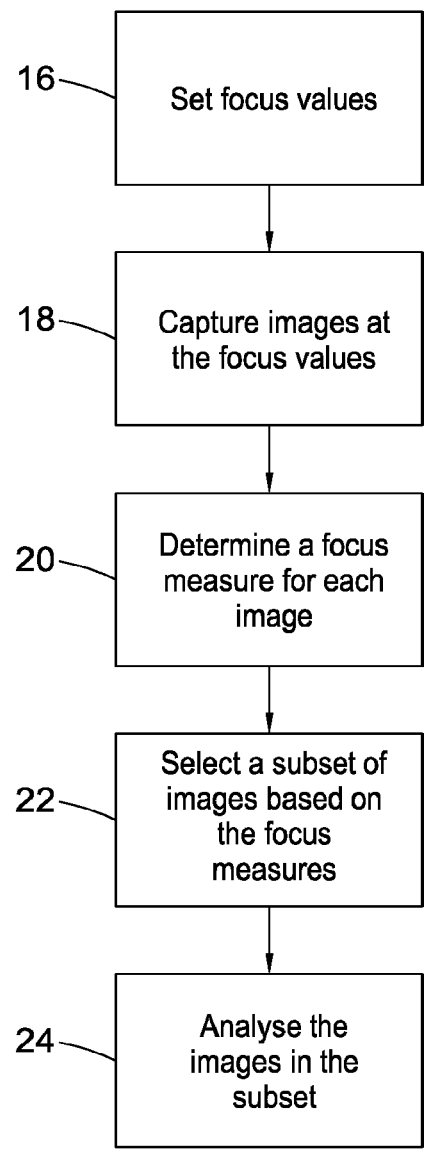
FIG. 2 is a schematic diagram of a method of acquiring and processing images of a flowing liquid sample.
Figure 3:
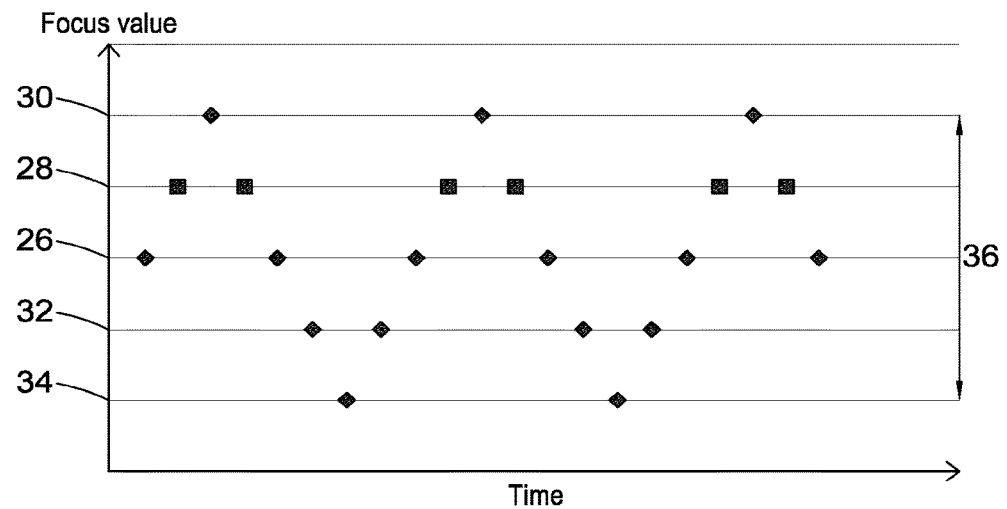
FIGS. 3-5 are schematic plots of focus values at which images are taken against time.

With reference to FIGS. 2 and 3, a method of capturing and processing images of a liquid sample during flow is described.

With reference to FIG. 2, at step 16, a plurality of focus values are determined. These are set based on characteristics of the flow channel and/or the imaging device. In some embodiments, the plurality of focus values are set such that the corresponding focal planes are evenly spaced across the full depth of the channel through which, in use, the liquid sample flows. In some embodiments, the plurality of focus values is set based on the hardware used and/or how fast the focus mechanism of the imaging device can be stepped through focus values. In some embodiments, the plurality of focus values is set based on an estimate of the minimum number of in-focus images needed to obtain an accurate cell count and/or the sensitivity of cell-counting algorithms used to the degree to which an image is in focus.

Alternatively, in some embodiments, step 16 may be omitted from the method and instead, pre-determined focus values may be used. In some embodiments, the plurality of focus values may be pre-determined experimentally, as will be described below.

At step 18, the processor causes the focus mechanism to step through the plurality of focus values and the imaging device to capture images while the focusing mechanism is stepped through the plurality of focusing values. A schematic diagram of a plot of focus value against time is shown in FIG. 3. Each point represents an image captured. As shown, the plurality of focus values comprises a starting focus value 26 and a number of other focus values 28, 30, 32 and 34 falling within a range 36. Typically, the range is on the scale of micrometers, e.g. 200-300 micrometers.

The processor sets the focus mechanism of the imaging device to the starting focus value 26 and causes the imaging device to capture an image. The processor then steps the focus mechanism to the next focus value 28, as shown in FIG. 3, and captures another images. This process is repeated, stepping the focus mechanism through the focus values and capturing an image at each focus value. In some embodiments, the time between each captured image is between 5 and 20 milliseconds. The rate at which images are captured may, in some embodiments, be limited by the frame rate of the imaging device (i.e. the number of images the imaging device can capture per time interval). In some embodiments, the rate at which images are captured may be limited by the speed at which the focus mechanism can be stepped through the focus values. In some embodiments, the focus mechanism may comprise a stepper motor which is used to vary the focus value. The rate at which images are captured may, in some embodiments, be limited by the characteristics, e.g. the speed, of the stepper motor.

In stepping through the plurality of focus values, the processor repeatedly varies the focus value between a minimum value 34 and a maximum value 30 in a periodic, oscillatory fashion, as illustrated in FIG. 3.

In some embodiments, the shape of the plot of focus value as a function of time may equally take any other shape. For example, it may take the form of a sawtooth, a sinusoid, or a step function. For the latter option, the method may comprise taking a plurality of images at a first focus value, then a second focus value, then a third focus value and so on, with the focus value increasing (or decreasing) over time.

In some embodiments, images are captured continuously (i.e. as often as the imaging device will allow) whilst the focus mechanism is varied between the minimum focus value 34 and the maximum focus value 30, for example in the way shown in FIG. 3.

At step 20, referring to FIG. 2, a focus measure is determined for each of the captured images. In some embodiments, a focus measure may be determined for only some of the captured images. For example, a focus measure may be determined for each image in the first one (or two or three) cycles over the set of focus values. Any suitable technique, as known in the art, may be used to determine a focus measure. The following methods are provided by way of example.

In some embodiments, a Sobel operator may be used to determine a focus measure for captured images. This may be suitable where the images include objects with a high contrast (relative to the image background). This technique may be used on images of white blood cells, for example, but may also be used in counting platelets or other objects. As a first step, each image is segmented into objects and background. An image patch is defined around each segmented object and a Sobel operator is convoluted with each image patch. The results of these convolutions are averaged over image patches to calculate the focus measure for that image.

In a specific implementation, the following Sobel operator and magnitude calculation is used to derive an average gradient magnitude as a focus measure for each image patch:

If each image patch is denoted by A, and Gx and Gy define two images patches which at each point contain the horizontal and vertical derivative approximations, the computations are as follows:

$$G_x = \begin{bmatrix} -1 & 0 & +1 \\ -2 & 0 & +2 \\ -1 & 0 & +1 \end{bmatrix} * A \text{ and } G_y = \begin{bmatrix} +1 & +2 & +1 \\ 0 & 0 & 0 \\ -1 & -2 & -1 \end{bmatrix} * A$$

where * denotes a 2-dimensional convolution operation.

At each pixel in the image, the resulting gradient approximations can be combined to give the gradient magnitude as the square root of the sum of the squares of Gx and Gy at the pixel, or the sum of the absolute values as an approximation. This quantity is then averaged or summed over the image patch pixels to give the focus measure.

The focus measure for the image patches within an image are then averaged in order to determine a single focus measure for that image.

In some embodiments, template matching techniques (as are known in the art) may be used to determine a focus measure for each image. Such techniques are described at https://en.wikipedia.org/wiki/Template_matching, for example. Template matching techniques may be suitable for images in which the contrast between the objects and the image background is relatively low. In some embodiments, template matching techniques may be used where the objects are platelets, for example where the images are captured for the purpose of determining a platelet count.

As a first step, an initial template is determined. The initial template is set based on what an in-focus object would look like in a captured image. This may be, for example, a circle with diameter equal to the average size of a platelet. This template is then applied to the images and a number of objects are identified. A similarly score for each object (i.e. a score based on the similarity of each object to the template) is determined and a threshold is applied to the similarity scores to determine those objects which are most similar to the initial template. The template is then adjusted based on the shape of the selected objects and the process repeated.

This process can be repeated a number of times, each time adjusting the template to fit the objects in the image, to obtain a final template for an in-focus object. This template is then applied to the images to identify the in-focus objects within each image. A focus measure for each image is then determined based on the number of in-focus images in each image. In particular, the more in-focus objects there are in an image, the better the focus measure for that image.

In some embodiments, other techniques may be used to determine a focus measure for each image, as is known in the art. In particular, in some embodiments, a measure of contrast between cells and the image background may be determined as part of determining a focus measure for an image.

At step 22, a subset of images for further processing is identified based on the focus measures determined at step 20. An ensemble measure of the focus measures is determined across images captured at each focus value, for example an average focus measure or a median focus measure, and the focus value with the best corresponding ensemble measure is selected. The images which were taken at the selected focus value are identified for further processing. In some embodiments, the average focus measure may be an extremum or a local extremum.

In some embodiments, identifying a subset of images for analysis involves selecting a focus value for which the corresponding average focus measure is a local extremum and the corresponding average object velocity is larger than object velocities at any other local extrema of the determined focus measures. Methods of determining object velocities are described in application number PCT/EP2015/072416, which is incorporated by reference herein in its entirety.

As mentioned above, in some embodiments, images taken at different focus values may be included in the subset of images identified for further processing. This may be useful, for example, where there are different groups of objects within a channel. For example, it may be desirable to obtain in-focus images of cells flowing along the channel at a depth halfway down the channel and also in-focus images of cells on the bottom of the channel.

In some embodiments, a subset of images for further processing is identified based on the focus measures of the captured images in other ways.

In some embodiments, images for further processing may be identified based directly on the focus measures of the images. For example, a criterion may be applied to the focus measure of each image and the images which have a focus measure which meets the criterion are included in the subset, i.e. are identified for further processing. In some embodiments, identifying a subset of the captured images includes applying a threshold to the determined focus measures for the images. For example, any images which have a focus measure above a given threshold may be selected. In some embodiments, identifying a subset of images for further processing includes determining a range of focus measures and identifying for further processing those images which have a focus measure falling within the range. This may be the interquartile range, for example, or may be a range between two pre-determined values. In some embodiments, identifying a subset includes placing the focus measures in numerical order and including in the subset those images which have a focus measure in a range of values, for example the top 5%, 10% or 20% etc. of focus measures.

In some embodiments, a subset of images may be identified for further processing based on the mean focus measure, the median focus measure, the standard deviation of the focus measures (e.g. across all captured images, or images taken at a particular focus value) or any other quantity.

In some embodiments, images may be identified for further processing based on the focus measures of the images indirectly. For example, one or more focus values may be selected based on the focus measures of images captured at that focus value or values. The images captured at that focus value or values may be identified for further processing.

As mentioned above, a focus measure may be identified for only some of the captured images. For example, a focus measure may be determined only for each image in the first one (or two or three etc.) cycles over the set of focus values, using any of the methods described above or by any other method. A focus value may then be selected based on the determined focus measures and each captured image which was taken when the focussing mechanism was set according to the selected focus value is identified for further processing. Objects may then be identified in each image in the subset identified for further processing using any suitable technique. For example, template matching techniques such as those described above may be used to identify objects in the images identified for further processing.

At step 24, the images of the subset are analysed. Analysing the images may include identifying and counting objects (for example cells or platelets) in the images.

In some embodiments, a platelet count is determined based on the subset of images, as will now be described.

Of the subset of images identified for further processing (which may comprise, in some embodiments, e.g. 5000 images), a subset of these images are selected based on the number of images required to provide an accurate count. For example, 100 images may be required to obtain an accurate platelet count result. Therefore, 100 images are selected from the subset identified for further processing. To avoid (or at least reduce the chances of) double-counting the objects (e.g. platelets) (i.e. to avoid counting a given object more than once because it appears in more than one image), the 100 images are selected such that they are evenly spaced (in time) across the subset identified for further processing. In this way, the chances of a given object being present in more than one image is reduced (or even eliminated).

Once the subset of the subset of images (i.e. the 100 images, in this example) have been selected, objects in the subset of subset of images are then identified, for example using standard techniques known in the art. In some embodiments, as mentioned above, template matching techniques (in line with those described above) may be used to identify objects. In some embodiments, objects in the images may have already been identified as part of determining a focus measure for each image (as described) above.

A check may then carried out to identify any objects stuck in the field of view of the imaging device (i.e. objects stuck in place in the field of view, rather than flowing along the flow channel). In other words, a check is carried out to identify any objects as having remained stationary during a period of time during which images were captured. This check is carried out to avoid double-counting any objects stuck in the field of view (or at least reduce the chances of double counting). For example, the images may be compared and any objects which appear in the same position in multiple images may be identified as being stuck and taken into account in determining the final object count.

In some embodiments, the check may comprise summing a plurality of images, for example by stacking the plurality of images on top of one another. In other words, an image may be produced in which each pixel has a brightness equal to the sum of the brightnesses of the pixels in the corresponding position in the plurality of images. In this way, any objects which are in the same position in a plurality of images will show up as an extremum (for example a local extremum or otherwise) in brightness in the image.

Next, the total number of objects in the subset of the subset of images (i.e. the 100 images) are counted (taking into account any objects which are stuck in the field of view). This total is then divided by the total volume of liquid appearing in the subset of the subset of images (i.e. the 100 images). The total volume of liquid can be calculated by multiplying the number of images in the subset of the subset (100, in this example) by the volume of liquid contained in the field of view of the imaging device. The volume of liquid contained in the field of view of the imaging device can be determined based on the dimensions of the field of view and optionally the dimensions of the flow channel.

For N images selected from the subset of images identified for further processing, an object count (such as a platelet count or a count of any other objects in the image, for example white or red blood cells) may be identified as follows:

$$C = \frac{\text{Total number of platelets in the } N \text{ images}}{N \ V_{FoV}}$$

Where $V_{FoV}$ is the volume contained in the field of view of the image capture device.

For the avoidance of doubt, although example figures of 5000 images in the subset identified for further processing and 100 images selected from that subset have been used above, the number of images captured and/or used may equally be different, in some embodiments. Any reference to 'object' made herein may refer to e.g. platelets, red blood cells or white blood cells.

In some embodiments, other methods may be used to count objects, for example platelets or blood cells, as are known in the art. An example of methods directed to the identification and counting of cells are set out in application number PCT/EP2015/072392, which is incorporated herein by reference in its entirety.

In some embodiments, as described above, the plurality of focus values at which images are captured comprises a starting focus value and a number of focus values falling within a range around the starting focus value. The starting focus value and the range may be determined experimentally, as will now be described.

Firstly, one or more calibration assays are carried out using one or more calibration disks. A different calibration disk is used for each assay and as part of each assay, a focussing algorithm is carried out in order to determine a suitable (e.g. optimal) focus value for each assay.

Using multiple calibration disks may be advantageous for the following reason. Due to imperfections in the manufacturing process used to manufacture the disks, each disk (and in particular, the microfluidic structures of each disk) may be slightly different. Further, the positioning of the disk relative to the image capture device (and in particular, the positioning of the flow channel relative to the image capture device) may be slightly different between disks. In embodiments in which a plurality of assays are carried out using a plurality of calibration disks, by determining a suitable (e.g. optimal) focus value for a plurality of calibration disks, these differences and imperfections in the manufacturing process can be taken into account in determining a starting focus value and a range of focus values, as will now be described.

The starting focus value and the range are set based on the determined focus values for the assays. In some embodiments, the starting value is an average of the determined focus values over the assays and the range is set so as that the determined focus value for each assay falls within the range.

In some embodiments, additionally or alternatively, the values, number and spacing (spacing in terms of focus value and/or in terms of time) may be determined based on other variables. Examples include the minimum number of images required to accurately determine the quantity to be determined (e.g. a blood cell count or platelet count), the range of suitable focus values determined for the calibration assays and the sensitivity of the degree to which images are in focus of the analysis algorithms used (e.g. cell identification and counting algorithms).

In some embodiments, the starting focus value and the range may be determined based on the dimensions of the channel through which, in use, the liquid sample flows and/or characteristics of the imaging device. For example, in some embodiments, the starting focus value may be set such that the corresponding focal plane is at a depth halfway down the channel and the range may be set so as to cover the full depth of the channel.

Figure 4:
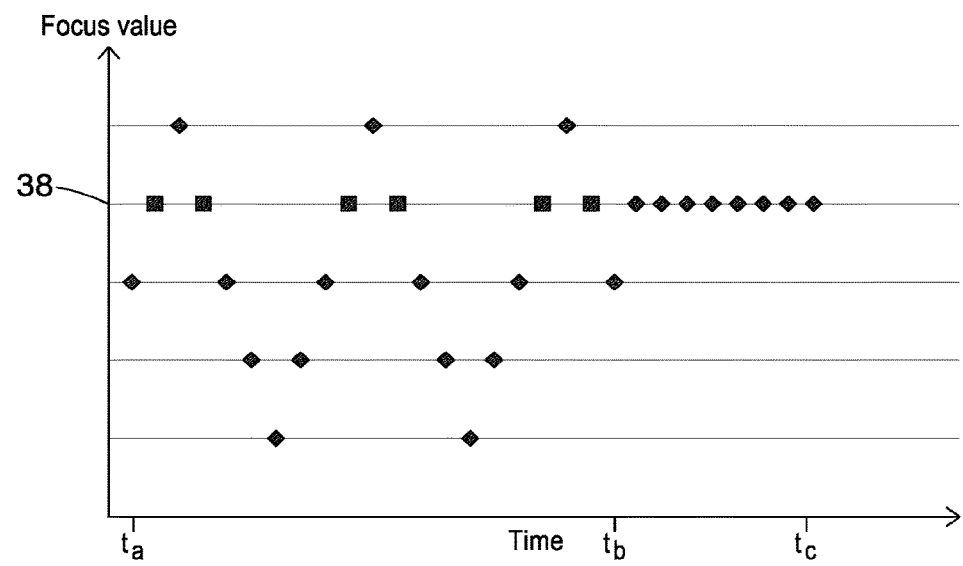

With reference to FIG. 4, in some embodiments, the above-described methods of taking multiple images at multiple focus values may be used to determine a focus value which is then used to take further images. In other words, a method may comprise the following steps:

Capturing a plurality of images at each of a plurality of focus values

Determining a focus measure for each image

Identifying a suitable focus value 38 based on the focus measures

Setting the focusing mechanism of the imaging device to the focus value 38

Capturing further images at the focus value 38

Identifying for further processing the images captured when the focusing mechanism was set to the suitable focus value (including the images taken before the suitable focus value was determined)

A schematic diagram of possible focus values at which images are taken over time using the above described method is shown in FIG. 4. As shown, the method comprises an initial stage of image capture, between $t_a$ and $t_b$ in which images are captured at a plurality of focus values. A suitable focus value 38 is then determined based on these images and the focus mechanism is set to the suitable focus value. Further images are then captured at the suitable focus value, between $t_b$ and $t_c$.

These two stages of image capture may be repeated. In other words, as mentioned above, the method may comprise alternating phases of (a) varying the focus value and capturing images and (b) keeping the focus value constant and capturing images. In this way, a check may be carried out periodically (by varying the focus value, capturing images and analysing the images) in order to check that images are being captured at a suitable focus value. If they are not, then the focus value of the focus mechanism may be changed accordingly.

Figure 5:
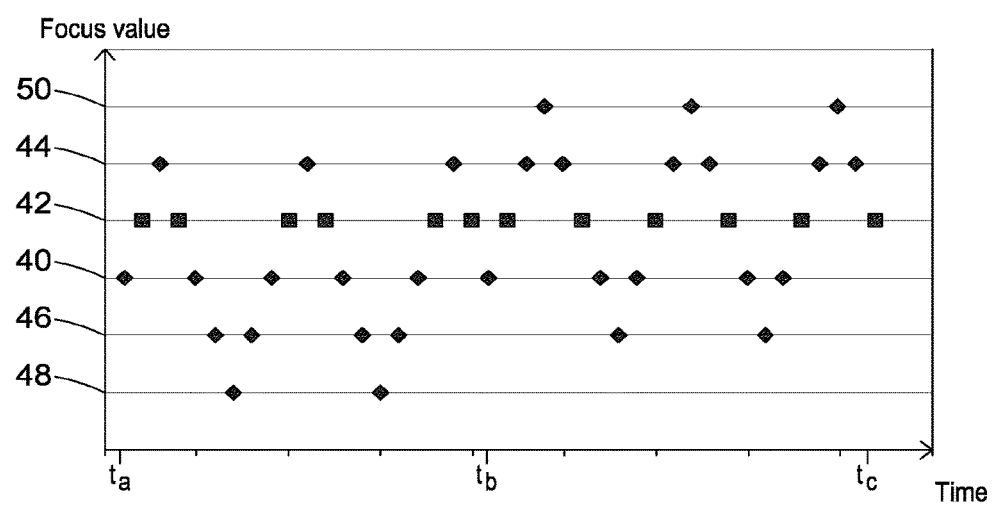

With reference to FIG. 5, in some embodiments, the plurality of focus values at which images are captured may be updated over time based on analysis of previously captured images. In some embodiments, a method comprises:

Setting a first plurality of focus values (40, 42, 44, 46 and 48)

Capturing images at the first plurality of focus values

Determining a focus measure for each image

Determining a suitable focus value 42 based on the focus measures

Setting a second plurality of focus values (42, 44, 50, 40 and 46) based on the determined suitable focus value.

In some embodiments, once a focus value has been selected, the starting focus value may be updated to the selecting focus value (i.e. from 40 to 42). In this way, the range of focus values at which images are captured may be shifted over time as the images taken previously are processed and the resulting data used to optimise the focus values at which later images are captured.

In some embodiments, this process may be repeated, with the starting focus value being updated periodically to optimise the focus values at which images are captured.

A schematic diagram of possible focus values at which images are taken over time using the above described method is shown in FIG. 5. As shown, the method comprises an initial stage of image capture, between $t_a$ and $t_b$ in which images are captured at a first plurality of focus values (40, 42, 44, 46 and 48). A suitable focus value 42 is then determined based on these images and the starting focus value is set to the suitable focus value 42. Further images are then captured at a second plurality of images falling in a range around the starting focus value, between $t_b$ and $t_c$.

As mentioned above, in some embodiments, the flow channel is provided on a cartridge or disc, such as a lab-on-a-chip device. Such a device may be a microfluidic device. The cartridge or disc may have an inlet via which a liquid sample, e.g. a blood sample, is inserted, the channel being in fluidic communication with the channel. In some embodiments, the cartridge or disc is inserted into a holder associated with the imaging device in order to fixedly dispose the flow channel relative to the imaging device.

Alternatively, in some embodiments, a flow channel and the imaging device may be provided as part of a single device.

In either case, in some embodiments, the depth of the flow channel in a direction perpendicular to the focal plane of the imaging device may be such that it accommodates a single layer of objects which move across the field of view of the imaging device.

It may be preferable to ensure that a single layer of objects move across the field of view of the image capture device to increase the chance that each object is imaged and optionally counted. It may also be preferable in order to facilitate the classification of the objects, for example as part of a cell classification process. If multiple layers of objects were provided in the field of view then some objects could be blocked from view completely and others could be partially obscured by other objects. Having a single layer of objects also facilitates any defining characteristics of objects (including cells) being captured. In some embodiments, the flow channel may be at least twice as wide as the estimated largest dimension of any object to be detected and its depth is less than twice this largest dimension. In some embodiments, the flow channel is between 2 and 15 mm long, between 0.18 mm and 0.8 mm wide and between 0.02 and 0.03 mm deep. In one embodiment, the flow channel is 15 mm long, 0.06 mm wide and 0.02 mm deep.

It will be appreciated that specific embodiments have been described by way of illustration only and that various modifications, alterations and juxtapositions of the described features are possible without departing from the invention, as described above and otherwise. In particular, the steps of the process described above with reference to FIG. 2 can to some extent be changed in order and may be grouped and combined as appropriate.

Whilst FIGS. 3, 4 and 5 illustrate a method of varying the focus value in a periodic fashion about a starting focus value, the shape of the plot of focus value as a function of time may equally take any other shape. For example, it may have the form of a sawtooth, a sinusoid, or a step function. For the latter option, the method may comprise taking a plurality of images at a first focus value, then a second focus value, then a third focus value and so on, with the focus value increasing (or decreasing) over time).

It should be understood that references made herein to images being in focus or the imaging device focussing on the liquid sample are not necessarily restricted to the images being precisely in focus or the imaging device being optimally focussed on the sample. What can be considered an acceptably focused image can change depending on the application, for example the exact assay being performed. For example, if cell shape is not critical, a non-optimally focused imaged might yield results identical to an optimally focused one. Accordingly, focus values and images can be selected based on the criteria dictated by the kind of assay and any reference to an optimal or suitable focus value may be any focus value adhering to the particular requirements of a given assay or process.

The various methods described above may be implemented by a computer program. The computer program product may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

Unless specifically stated otherwise, as apparent from the following discussion, it is appreciated that throughout the description, discussions utilizing terms such as "receiving", "determining", "comparing", "enabling", "maintaining," "identifying," or the like, may refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Further, the described methods can be implemented using any suitable stand-alone or distributed computing environment using any suitable computing platform or processor, for example an integrated circuit, self-contained or in combination with other components of the system, a dedicated computing device housed on an appropriate card together with the other components of the system or otherwise, a standalone computing device such as a personal computer, tablet computer or mobile phone or a server which performs the necessary processes at least in part remotely exchanging data over a network connection.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of capturing images of a liquid sample flowing through a channel on a microfluidic cartridge, wherein the channel passes through a field of view of an imaging device, the method comprising:
   retaining the microfluidic cartridge relative to the imaging device such that the channel is disposed relative to the field of view;
   stepping a focus mechanism of the imaging device through a first plurality of focus values;
   capturing a plurality of images of the sample at each of the first plurality of focus values as the sample flows through the channel passing through the field of view of the imaging device to obtain a set of images of the liquid sample over time for each of the plurality of focus values;
   determining a focus measure for each of the captured images; and
   identifying for further processing a subset of the captured images based on the determined focus measures.

2. The method of claim 1 wherein stepping the focus mechanism through the first plurality of focus values comprises repeatedly varying the focus value between a minimum value and a maximum value.

3. The method of claim 1, wherein identifying a subset of the captured images comprises evaluating a criterion on the focus measure for each captured image and identifying for further processing images with a focus measure which meets the criterion.

4. The method of claim 1, comprising:
   identifying a first focus value based on the focus measures;
   setting the focusing mechanism of the imaging device to the first focus value; and
   capturing further images at the first focus value.

5. The method of claim 4, comprising identifying for further processing images captured when the focusing mechanism was set to the first focus value.

6. The method of claim 4, comprising:
   (a) stepping the focus mechanism of the imaging device through a second plurality of focus values;
   (b) capturing a plurality of images of the sample at each of the second plurality of focus values as the sample flows through the field of view of the imaging device;
   (c) determining a focus measure for each of the images captured at each of the second plurality of focus values;
   (d) identifying a second focus value based on the focus measures determined in step (c);
   (e) setting the focusing mechanism of the imaging device to the second focus value; and
   (f) capturing further images at the second focus value.

7. The method of claim 6, comprising identifying for further processing images captured when the focusing mechanism was set to the second focus value.

8. The method of claim 1, comprising:
   determining a focus value based on the determined focus measures;
   setting a second plurality of focus values based on the determined focus value;
   stepping the focus mechanism of the imaging device through the second plurality of focus values; and
   capturing a plurality of images of the sample at each of the second plurality of focus values as the sample flows through a field of view of the imaging device.

9. The method of claim 1, comprising further processing the images in the subset.

10. The method of claim 9, wherein further processing the images comprises determining a characteristic of the liquid sample or a component of the liquid sample based on the images in the subset.

11. A system for capturing images of a liquid sample, the system comprising:
   a flow channel through which the liquid sample flows;
   an imaging device configured such that the liquid sample flows through a field of view of the imaging device; and
   a processor operably controlling the imaging device so as to implement a method as claimed in claim 1.

* * * * *